(12) United States Patent
Schlezinger et al.

(10) Patent No.: US 9,341,580 B2
(45) Date of Patent: May 17, 2016

(54) LINEAR INSPECTION SYSTEM

(71) Applicant: Applied Materials, Inc., Santa Clara, CA (US)

(72) Inventors: Asaf Schlezinger, Sunnyvale, CA (US); Shengde Zhong, Xi'an (CN)

(73) Assignee: APPLIED MATERIALS, INC., Santa Clara, CA (US)

( * ) Notice: Subject to any disclaimer, the term of this patent is extended or adjusted under 35 U.S.C. 154(b) by 53 days.

(21) Appl. No.: 14/493,824

(22) Filed: Sep. 23, 2014

(65) Prior Publication Data

US 2015/0377796 A1    Dec. 31, 2015

Related U.S. Application Data

(60) Provisional application No. 62/018,300, filed on Jun. 27, 2014.

(51) Int. Cl.

| G01N 21/00 | (2006.01) |
|---|---|
| G01N 21/95 | (2006.01) |
| G01N 21/64 | (2006.01) |
| G01R 31/26 | (2014.01) |
| H02S 50/15 | (2014.01) |
| H02S 50/10 | (2014.01) |

(52) U.S. Cl.
CPC ............ G01N 21/9501 (2013.01); G01N 21/64 (2013.01); G01R 31/2601 (2013.01); H02S 50/10 (2014.12); H02S 50/15 (2014.12); *G01N 2201/0612* (2013.01)

(58) Field of Classification Search
CPC ... H01J 37/32935; G01N 21/68; G01N 21/64; G01N 2015/1037; G01N 21/0501; G01J 3/02; H02S 50/00; H02S 50/10; H02S 50/15
USPC .................................. 356/72–73, 300–445
See application file for complete search history.

(56) References Cited

U.S. PATENT DOCUMENTS

| 4,454,472 A | 6/1984 | Moore |
| 5,386,119 A | 1/1995 | Ledger |

(Continued)

FOREIGN PATENT DOCUMENTS

| EP | 0416787 A1 | 3/1991 |
| EP | 2781912 A1 | 9/2014 |

(Continued)

OTHER PUBLICATIONS

PCT/US2015/034045, mailed Aug. 31, 2015, International Search Report and Written Opinion.

*Primary Examiner* — Abdullahi Nur
(74) *Attorney, Agent, or Firm* — Patterson & Sheridan, LLP

(57) ABSTRACT

Embodiments of the disclosure generally relate to comprehensive, expandable substrate inspection systems. The inspection systems include multiple metrology units adapted to inspect, detect, or measure one or more characteristics of a substrate, including thickness, resistivity, saw marks, geometry, stains, chips, micro cracks, crystal fraction, and photoluminescence. The inspection systems may be utilized to identify defects on substrates and estimate solar cell efficiency of a solar cell produced with the substrate, prior to processing a substrate into a solar cell. Substrates may be transferred through the inspection system between metrology units on a track or conveyor, and then sorted based upon inspection data.

20 Claims, 7 Drawing Sheets

(56) References Cited

U.S. PATENT DOCUMENTS

| | | | |
|---|---|---|---|
| 5,396,332 A | 3/1995 | Ciszek | |
| 5,716,876 A | 2/1998 | Muramatsu | |
| 5,909,282 A | 6/1999 | Kulawiec | |
| 6,903,446 B2 | 6/2005 | Tuttle et al. | |
| 7,171,035 B2 | 1/2007 | Guldi et al. | |
| 8,629,411 B2 | 1/2014 | Beck et al. | |
| 2005/0118938 A1* | 6/2005 | Mizomoto | B24B 37/345 451/65 |
| 2014/0212020 A1 | 7/2014 | Weber | |

FOREIGN PATENT DOCUMENTS

| | | | |
|---|---|---|---|
| KR | 1020070099495 | | 12/2007 |
| KR | 1020110035845 | | 4/2012 |
| KR | 1020130073074 | | 7/2013 |
| KR | 1020120116517 | | 8/2013 |
| KR | 1020090066632 | | 1/2014 |
| WO | 8401212 | A1 | 3/1984 |
| WO | 03036718 | A2 | 5/2003 |
| WO | 2013080093 | A1 | 6/2013 |
| WO | 2014147467 | A1 | 9/2014 |

* cited by examiner

LINEAR INSPECTION SYSTEM

CROSS-REFERENCE TO RELATED APPLICATIONS

This application claims benefit of U.S. Provisional Patent Application Ser. No. 62/018,300, filed Jun. 27, 2014, which is herein incorporated by reference.

BACKGROUND

1. Field

Embodiments of the disclosure generally relate to an inspection system for inspecting substrates, such as semiconductor substrates.

2. Description of the Related Art

Substrates, such as semiconductor substrates, are routinely inspected during processing at independent inspection stations to ensure compliance with predetermined quality control standards. Different inspection techniques provide comprehensive data regarding products and processes. However, comprehensive inspections can be time consuming, thus reducing throughput, due to the number of inspection stations required and the resulting transfer time of moving substrates therebetween. Thus, device manufacturers are often faced with the decision of choosing between thorough inspections with burdensome inspection/transfer times, or foregoing certain inspection processes.

Therefore, there is a need for a substrate inspection system capable of quickly and comprehensively inspecting substrates.

SUMMARY

Embodiments of the disclosure generally relate to comprehensive, expandable substrate inspection systems. The inspection systems include multiple metrology units adapted to inspect, detect, or measure one or more characteristics of a substrate, including thickness, resistivity, saw marks, geometry, stains, chips, micro cracks, and crystal fraction. The inspection systems may be utilized to identify defects on substrates and estimate cell efficiency prior to processing a substrate. Substrates may be transferred through the inspection system between metrology units on a track or conveyor, and then sorted into respective bins based upon inspection data.

In one embodiment, an inspection system comprises a front end including a robot adapted to unload substrates from a cassette and load the substrates onto a conveyor and a modular unit including one more metrology units linearly disposed along the conveyor. The one or more metrology units are adapted to inspect substrates transferred by the conveyor. The one or more metrology units include a micro-crack inspection unit, a thickness measurement unit, a photoluminescence unit, a geometry inspection unit, and a saw mark detection unit. The inspection system further includes a yield analysis server adapted to receive and process inspection data from the metrology units, and a sorting unit adapted to sort substrates based upon the inspection data.

In another embodiment, an inspection system comprises a front end including a robot adapted to unload substrates from a cassette and load the substrates onto a conveyor, and a modular unit including one more metrology units linearly disposed along the conveyor. The one or more metrology units are adapted to inspect substrates transferred by the conveyor. The one or more metrology units include a micro-crack inspection unit, and a thickness measurement unit capable of measuring substrate thickness with a repeatability of 0.5 microns or less and capable of measuring substrate resistivity with a repeatability of 1 percent less. The one or more metrology units also include a photoluminescence unit, a geometry inspection unit capable of measuring substrate length with repeatability of less than about 10 microns, and a saw mark detection unit. The geometry inspection unit includes a pair of U-shaped detectors. The inspection system also includes a yield analysis server adapted to receive and process inspection data from the metrology units, and a sorting unit adapted to sort substrates based upon the inspection data. The yield analysis server is adapted to generate a 3-dimensional virtual reconstruction of a brick or ingot from which the substrates were cut using inspection data received from the photoluminescence unit.

In another embodiment, an inspection system comprises a front end including a robot adapted to unload substrates from a cassette and load the substrates onto a first conveyor, and a modular unit including one more metrology units linearly disposed along the first conveyor. The one or more metrology units are adapted to inspect substrates transferred by the first conveyor. The one or more metrology units include a micro-crack inspection unit, and a thickness measurement unit capable of measuring substrate thickness with a repeatability of 0.5 microns or less and capable of measuring substrate resistivity with a repeatability of 1 percent less. The one or more metrology units also include a photoluminescence unit, a saw mark detection unit, and a geometry inspection unit. The geometry inspection unit is capable of measuring substrate length with repeatability of less than about 10 microns, capable of measuring substrate width with repeatability of less than about 40 microns, and capable of measuring substrate orthogonality with repeatability of about 0.1 degrees or less. The geometry inspection unit includes a pair of U-shaped detectors. The inspection system also includes a yield analysis server adapted to receive and process inspection data from the metrology units. The yield analysis server is adapted to generate a 3-dimensional virtual reconstruction of a brick or ingot using inspection data received from the photoluminescence unit. The inspection system also includes a sorting unit adapted to sort substrates based upon the inspection data. The sorting unit includes a second conveyor, a plurality of bins disposed laterally outward of edges of the second conveyor, and a plurality of sorting mechanisms for transferring substrates from the second conveyor to the plurality of bins.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the disclosure generally relate to comprehensive, expandable substrate inspection systems. The inspection systems include multiple metrology units adapted to inspect, detect, or measure one or more characteristics of a substrate, including thickness, resistivity, saw marks, geometry, stains, chips, micro cracks, crystal fraction, and photoluminescence. The inspection systems may be utilized to identify defects on substrates and estimate solar cell efficiency of a solar cell produced with the substrate, prior to processing a substrate into a solar cell. Substrates may be transferred through the inspection system between metrology units on a track or conveyor, and then sorted based upon inspection data. The systems of the present disclosure may be utilized for inspection of substrates including semiconductor wafers and solar cells; however, the inspection of other types of substrates is also contemplated.

Figure 1:
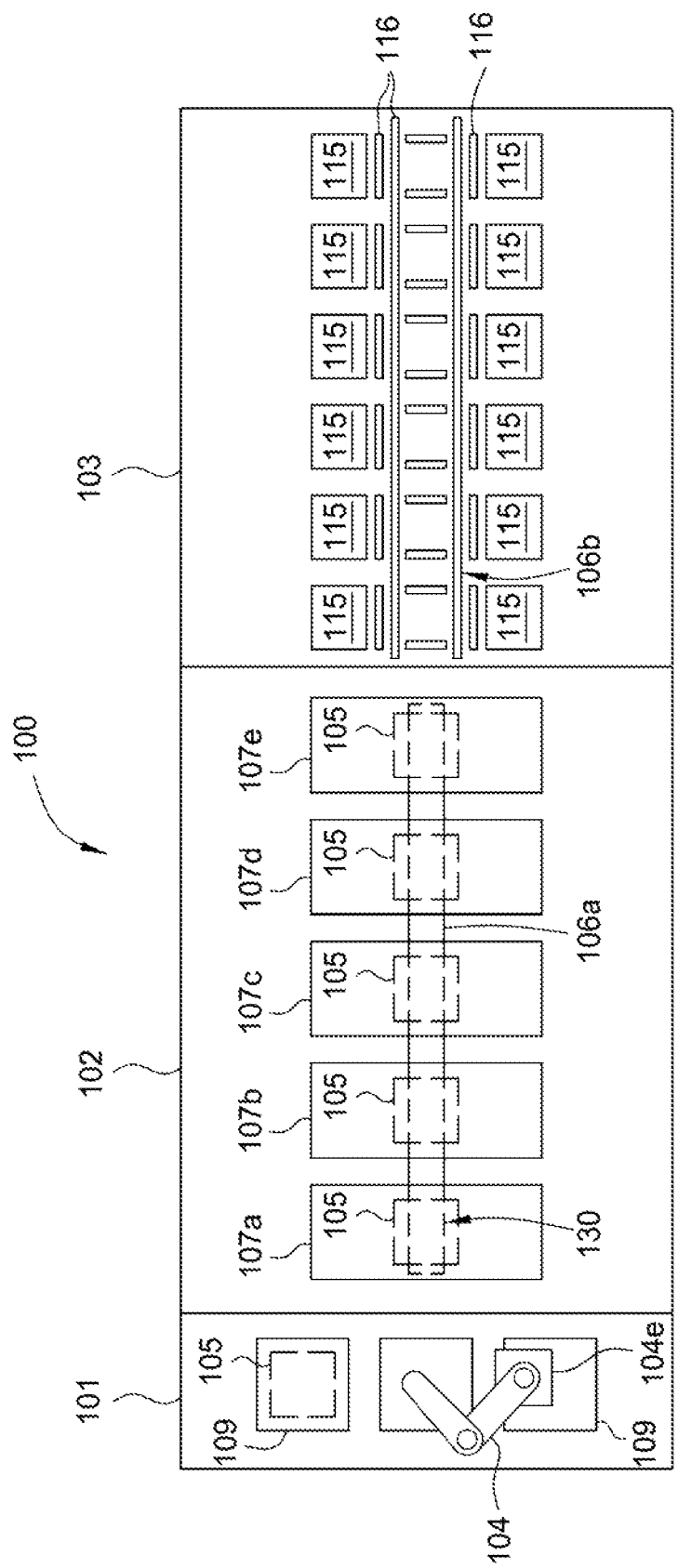
FIG. 1 illustrates a top plan view of an inspection system, according to one embodiment.

FIG. 1 illustrates a top plan view of an inspection system 100, according to one embodiment. The inspection system 100 includes a front end 101, a modular unit 102, and a sorting unit 103 disposed linearly relative to another. The front end 101 includes a transfer robot 104 having a support element 104e, such as a suction element, end effector, gripper or clamp, for gripping and transferring substrates 105. The transfer robot 104 is adapted to transfer substrates 105 from one or more cassettes 109 positioned within the front end 101 to a conveyor system 130. The conveyor system 130 may be a motor-driven conveyor system including one or more conveyors 106a, 106b such as belts or tracks (two are shown) driven by an actuator through rollers and/or drive gears. The conveyors 106a, 106b are disposed sequentially in a linear (in line) arrangement to transfer substrates 105 received from the transfer robot 104 through the modular unit 102 and to a location within the sorting unit 103. In the embodiment shown, the conveyors 106a, b are disposed sufficiently close to one another to allow a substrate to bridge the gap therebetween, or a roller (not shown) may be positioned between the belts to support a substrate between the belts and thus facilitate substrate transfer therebetween.

The conveyor 106a is disposed within the modular unit 102 and facilitates transfer of substrates 105 through the modular unit 102. Additional modular units may be positioned between the front end 101 and the modular unit 102, or between the modular unit 102 and the sorting unit 103, to facilitate expansion of the inspection system 100. One or more conveyors of the conveyor system 130 may then be replaced to accommodate the additional modular unit. Each of the modular units may include one or more metrology units. In the embodiment of FIG. 1, the modular unit 102 includes five metrology units 107a-e. It is contemplated that the inspection system 100 may also be modified by adding additional metrology units to the modular unit 102, as space permits, rather than adding a second modular unit, thus increasing throughput and/or characteristics evaluated.

In one example, the metrology unit 107a is micro-crack inspection unit adapted to inspect substrates 105 for cracks, as well as to optionally determine crystal fraction of a substrate 105. The metrology unit 107a is positioned adjacent to the front end 101 and is configured to accept substrates 105 positioned on the conveyor system 130 by the transfer robot 104. The substrates 105 are moved relative to the metrology unit 107a in a continuous manner as inspection, such as micro-crack detection, occurs.

The metrology unit 107b may be a thickness measuring unit adapted to measure both substrate thickness as well as resistivity of a substrate 105. The metrology unit 107b receives substrates 105 transferred along the conveyor 106a subsequent to inspection in the metrology unit 107a. The metrology unit 107b is disposed along the in line path of the substrates 105 defined by the conveyor 106a downstream of the location of the metrology unit 107a, and the metrology unit 107b performs one or more inspection processes on a substrate 105 as the substrate 105 is transferred relative thereto. The inspection process occurring at the metrology unit 107b is performed while the substrate is in motion; however, it is contemplated that the motion of the substrate 105 may be halted to facilitate increased accuracy of inspection.

The metrology unit 107c may be a photoluminescence unit configured to detect defects, perform impurity measurements (e.g., percentage of impurities), and crystal dislocation measurements. The metrology unit 107c receives substrates 105 transferred along the conveyor system 130 subsequent to inspection thereof in the metrology unit 107b. The metrology unit 107c is disposed along the in line path of the substrates 105 defined by the conveyor 106a downstream of the location of the metrology units 107a, 107b and the metrology unit 107c performs one or more inspection processes on a substrate 105 as the substrate 105 is transferred relative thereto. The inspection process occurring at the metrology unit 107c is performed while the substrate 105 is in motion; however, it is contemplated that the motion of the substrate 105 may be halted to facilitate increased accuracy of inspection.

Metrology unit 107d may be a geometry inspection unit configured to analyze the geometry and surface properties of a substrate 105. The metrology unit 107d receives substrates 105 transferred along the conveyor system 130 subsequent to inspection in the metrology unit 107c. The metrology unit 107d is disposed along the in line path of the substrates 105 defined by the conveyor 106a downstream of the location of the metrology units 107a-c, and the metrology unit 107d performs one or more inspection processes on a substrate 105 as the substrate 105 is transferred relative thereto. The inspection process occurring at the metrology unit 107d is performed while the substrate 105 is in motion; however, it is contemplated that the motion of the substrate 105 may be halted to facilitate increased accuracy of inspection.

The metrology unit 107e may be a saw mark detection unit. The saw mark detection unit is configured to perform on the fly inspection of saw mark depth and location, and may inspect and identify saw marks including groove, step, and double step. The metrology unit 107e is disposed along the in line path of the substrates defined by the conveyor 106a downstream of the location of the metrology units 107a-d, and the metrology unit 107e performs one or more inspection processes on a substrate 105 as the substrate 105 is transferred relative thereto. The inspection process occurring at the metrology unit 107e is performed while the substrate 105 is in motion; however, it is contemplated that the motion of the substrate 105 may be halted to facilitate increased accuracy of inspection.

The conveyor system 130 conveys the inspected substrates form the modular unit 102 to the sorting unit 103. The sorting unit 103 includes a conveyor 106b disposed longitudinally therethrough. As shown in FIG. 1, the conveyor 106b may include one or more conveyor belts (two are shown). One or more bins 115 (twelve are shown) are disposed laterally outward of the conveyor 106b. In the embodiment shown in FIG. 1, six bins 115 are disposed longitudinally on each side of the conveyor 106b in two parallel rows. The bins 115 are substantially equidistant from an edge of the conveyor 106b. The bins 115 are adapted to receive substrates 105 from the conveyor 106b. The substrates 105 may be sorted into the bins 115 according to characteristics determined during inspection processes performed in the metrology units 107a-e. Sorting mechanisms 116 are adjacent each bin 115 and the conveyor 106b to facilitate sorting of substrates 105 into bins 115. The sorting mechanisms 116 include a plurality of belts or rollers adapted to vertically actuate to lift a substrate 105 from the conveyor 106b and transfer the substrate 105 into a selected one of the bins 115 without stopping the motion of the conveyor 106b.

Although not shown, is contemplated that an additional bin 115 may be positioned at the end of and in line with the conveyor 106b to capture substrates 105 which may inadvertently be omitted from sorting, thus preventing damage to such substrates. While 12 bins 115 are shown, it is contemplated that more or less than 12 bins 115 may be included, such as 6, 18, or 24 bins.

While FIG. 1 discloses one embodiment of the inspection system 100, other embodiments are also contemplated. For example, while the conveyor system 130 includes two conveyors 106a, b, it is contemplated that the conveyor system 130 may include a single conveyor capable of transporting substrates 105 continuously through the inspection system 100. Alternatively, more than two conveyors 106a, b may be utilized.

Additionally, it is contemplated that the metrology units 107a-e may be duplicates of one another. For example, it is contemplated that the inspection system 100 may include duplicative micro-crack inspection units, thickness measuring units, photoluminescence units, geometry inspection units, or saw mark detection units, to increase throughput. In another embodiment, it is contemplated that the metrology units 107a-e may be configured in a linear arrangement or operational order other than described with respect to FIG. 1. In another embodiment, it is contemplated that one or more of the metrology units 107a-e may be replaced with a minority charge carrier inspection unit. In another embodiment, it is contemplated that a minority charge carrier inspection unit may be added as a sixth metrology unit. In yet another embodiment, it is contemplated that the front end may not include a robot 104. Rather, substrates 105 may be positioned on the conveyor system 130 by positioning a cassette adjacent the conveyor 106a. The cassette may then be indexed such that a substrate within the cassette contacts the conveyor 106a and is removed from the cassette onto the conveyor 106a due to relative motion therebetween. Further indexing may facilitate removal of additional substrates.

Figure 2:
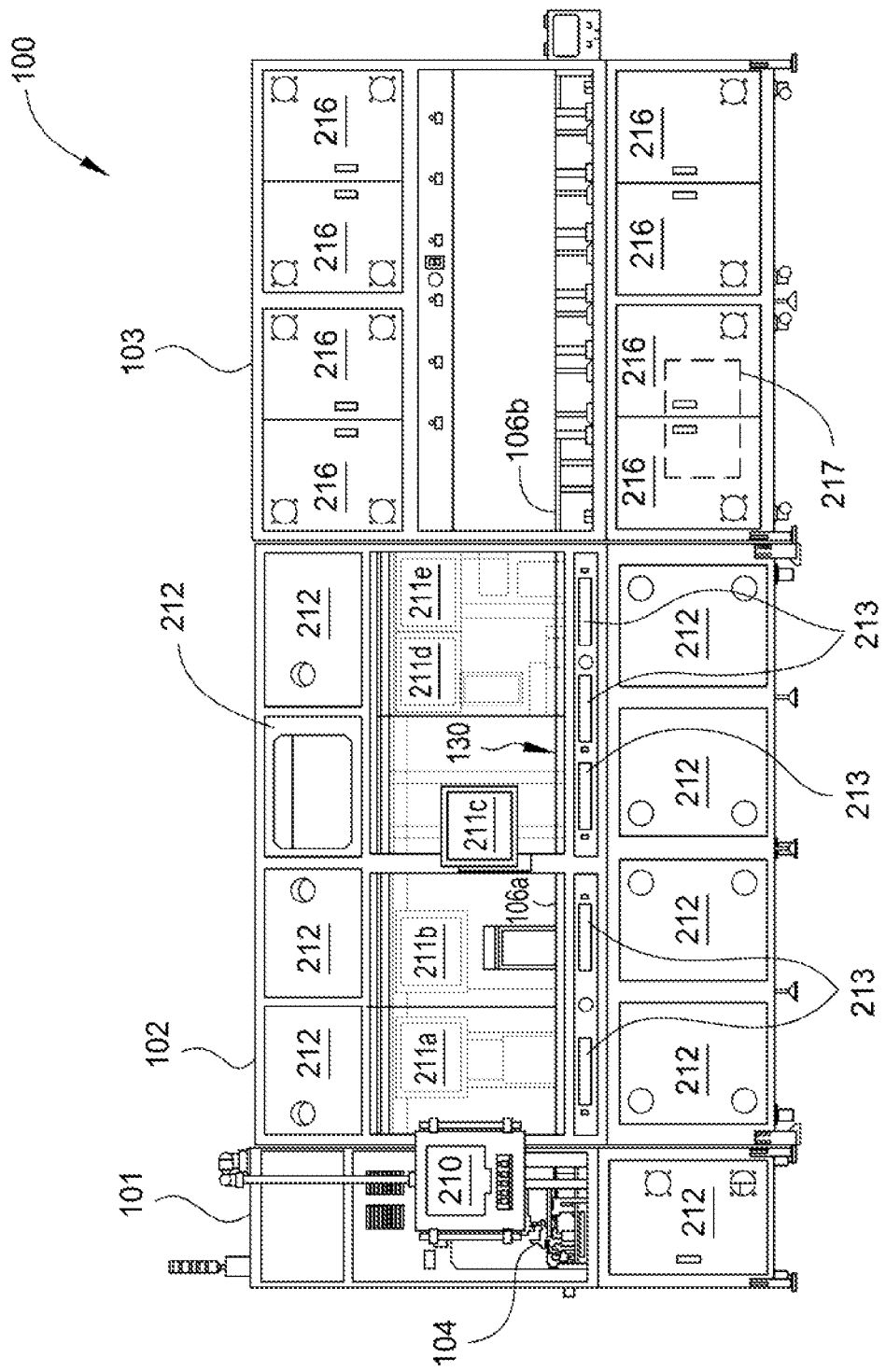
FIG. 2 illustrates a side view of the inspection system of FIG. 1.

FIG. 2 illustrates a side view of the inspection system 100 of FIG. 1. As illustrated, the front end 101, the modular unit 102, and the sorting unit 103 are arranged in a co-linear configuration such that substrates 105 (shown in FIG. 1) are transported along a generally straight line path through the system in a continuous manner on a conveyor system 130 for inspection. The front end 101 receives one or more cassettes containing substrates in a coin-stacked configuration, e.g., each cassette includes a plurality of slots therein, each slot configured to hold a substrate, and the cassette is positioned such that the substrates are positioned one over the other. The substrates are transferred from the cassettes via a robot 104 to the conveyor system 130 for transfer through the system 100. The front end 101 includes a computer 210 having a graphical user interface adapted to present information related to operations occurring in the front end, including metrics, lot numbers, and the like. In one example, the computer 210 may include a touch screen interface.

Each of the metrology units 107a-e (shown in FIG. 1) is also provided with a corresponding computer 211a-e having a graphical user interface and adapted to present information related to operations occurring at a respective unit. For example, the computers 211a-e may present one or more of images, graphs, tables, or other data. The computers 211a-e may also include touch screen interfaces. Each of the computers 210 and 211a-e may facilitate interaction with a respect front end 101 or metrology unit 107a-e for adjusting process parameters or conditions thereof.

The conveyor system 130 is a linearly disposed system of belts adapted to transport substrates to positions adjacent to the metrology units 107a-e for inspection of the substrates therewith. As illustrated in FIG. 2, the conveyor system 130 is disposed proximate to each of the metrology units 107a-e to facilitate transfer of the substrates adjacent inspection equipment, such as sensors or cameras, of each of the metrology units 107a-e. The modular unit 102 and the front end 101 may be provided with one or more access panels 212 at upper and/or lower ends thereof to facilitate access to the metrology units 107a-e and the front end 101 for maintenance. The modular unit 102 may also include one or more access ports 213 to further facilitate access to the metrology units 107a-e, to facilitate access to the conveyor system 130, to remove substrates during process, and the like.

The sorting unit 103 is disposed downstream of the metrology units 107a-e and is adapted to receive and sort substrates 105 based upon data from the metrology units 107a-e. A conveyor 106b positioned therein transfers substrates adjacent bins 115 for sorting of substrates thereto. The sorting unit 103 includes a plurality of access panels 216 (8 are shown) to facilitate maintenance of hardware of the sorting unit 103. As illustrated in FIG. 2, access panels 216 are disposed above the conveyor 106b at an upper portion of the sorting unit 103, while four access panels 216 are disposed beneath the conveyor 106b at a lower portion of the sorting unit 103. The sorting unit 103 may also include a yield analysis server 217 accessible by one or more access panels 216. Alternatively, it is contemplated that the yield analysis server 217 may disposed in the modular unit 102 and accessible through one or more access panels 212.

The yield analysis server 217 is coupled to one or more of the front end 101 and the metrology units 107a-e, and adapted to receive, collect, analyze, store, and/or report data received from the front end 101 and the one or more metrology units 107a-e with respect to each substrate passing therethrough. Additionally, the system user may provide data relating to the substrates, including the silicon brick from which the substrate was cut and the location of the substrate within the brick, as well as the location of the brick in the ingot from which it was cut. The yield analysis server 217 is capable of tracking inspection data over a predetermined interval, and may generate daily or long term graphs and statistics based upon the inspection data. Additionally, the yield analysis server 217 may track data and group data for substrates processed in a particular furnace, processing chamber, or machined with the same saw. Similarly, the yield analysis server may track and group data for substrates from the same ingot or brick, or for substrates produced from the same relative location within separate ingots. Monitoring and processing of data via the yield analysis server 217 facilitates identification and correction of quality control issues within a fabrication process. For example, the yield analysis server 217, and software thereon, may identify a silicon casting tool, or a particular oven, saw, or other tool which processes the greatest number of defective substrates, and conversely, the productivity of each casting tool, oven, saw, or other tool. Also, the yield analysis server may also track overall production values for a fabrication plant.

Sample data generated by the yield analysis server 217 may include: maximum and minimum thickness variation (TV) per saw; total thickness variation (TTV) in the X and Y directions per saw; mean TTV per saw; maximum and minimum resistivity per brick; TV yield per saw and lot; TV yield loss per saw; photoluminescence defects and impurity per brick; impurity location per brick; defect location per brick; and photoluminescence defect and impurity information per oven and per lot.

Figure 3:
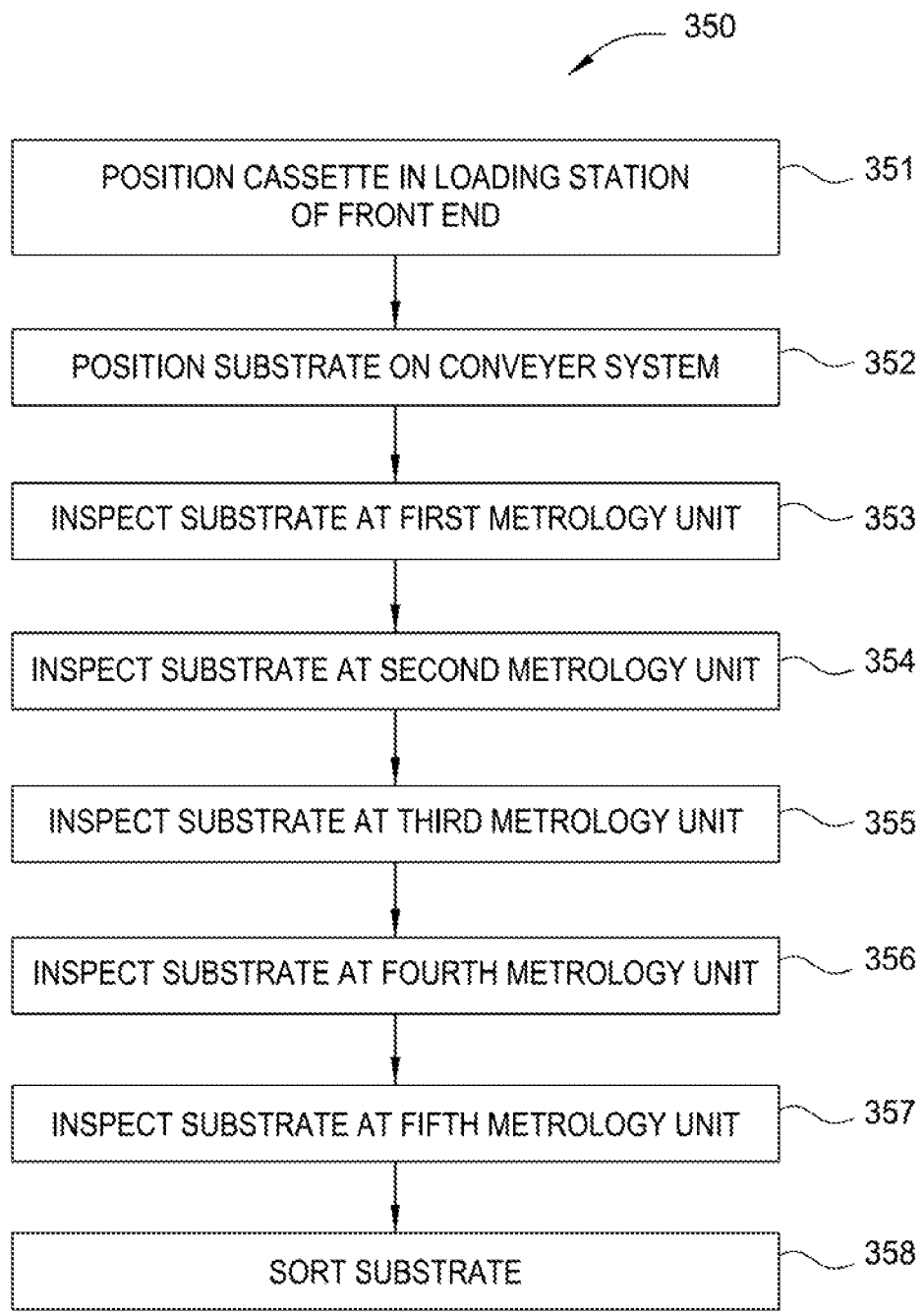
FIG. 3 illustrates a flow diagram of a method of inspecting a substrate, according to one embodiment.

FIG. 3 illustrates a flow diagram 350 of a method of inspecting a substrate, according to one embodiment. Flow diagram 350 begins at operation 351, in which a cassette carrying a plurality of substrates for inspection is positioned at a loading station of a front end, such as front end 101 of the inspection system 100. In operation 352, a robot located within the front end removes a substrate from the cassette and positions the substrate on a conveyor system, such as the conveyor system 130. As the conveyor system 130 moves through the inspection system 100, the conveyor system 130 transfer the substrate to each of a plurality of metrology units disposed along the conveyor system 130.

In operation 353, the substrate is positioned adjacent to, and inspected by, a first metrology unit, such as metrology unit 107a. In one example, the metrology unit 107a may be a micro-crack inspection unit. The micro-crack inspection unit may perform one or more operations on the substrate as the substrate is moved relative thereto, and then forward inspection data to a yield analysis server 217. In operation 354, the substrate is positioned adjacent to, and inspected by, a second metrology unit 107b as the substrate is transferred along the conveyor system 130. In one example, the metrology unit 107b may be a thickness and resistance measurement unit. The thickness and resistance measurement unit may perform one or more operations on the substrate as the substrate is moved relative thereto, and then forward inspection data to a yield analysis server 217.

In operation 355, the substrate is positioned adjacent to, and inspected by, a third metrology unit, such as metrology unit 107c. In one example, the metrology unit 107c may be a photoluminescence unit. The photoluminescence unit may perform one or more operations on the substrate as the substrate is moved relative thereto, and then forward inspection data to a yield analysis server 217. In operation 356, the substrate is positioned adjacent to, and inspected by, a fourth metrology unit, such as metrology unit 107d. In one example, the metrology unit 107d may be a geometry unit. The geometry unit may perform one or more operations on the substrate as the substrate is moved relative thereto, and then forward inspection data to a yield analysis server 217.

In operation 357, the substrate is positioned adjacent to, and inspected by, a fifth metrology unit, such as metrology unit 107e. In one example, the metrology unit 107e may be a saw mark inspection unit. The saw mark inspection unit may perform one or more operations on the substrate as the substrate is moved relative thereto, and then forward inspection data to a yield analysis server 217.

In operation 358, the substrate is transferred to a sorting unit, such as sorting unit 103, for sorting into a bin based upon the inspection data obtain in one or more of operations 352-357. The yield analysis server analyzes received inspection data and determines a particular bin in which the substrate is to be sorted. As the substrate is positioned adjacent to the appropriate bin, a sorting mechanism actuates to transfer the substrate from the conveyor system to the appropriate bin.

FIG. 3 illustrates one embodiment of a flow diagram 350; however, other embodiments are also contemplated. For example, it is contemplated that one or more of operations 353-357 may be omitted depending on the number of metrology units in the inspection system 100. It is also contemplated that additional inspection operations may be added to the flow diagram 350 if the inspection system 100 includes more than five metrology units. Additionally, it is contemplated that one or more subsequent inspection operations may be omitted due to inspection results obtained during a previous inspection operation. For example, if in operation 353 the first metrology unit determines that a substrate is defective, operations 354-357 may be omitted, and the substrate may proceed to the sorting bin corresponding to defective substrates. In another embodiment, operation 351 may include providing substrate identification information to the yield analysis server 217. The substrate identification information may include one or more of lot identification, substrate identification, cassette identification, and the like, which facilitates tracking of substrates though the inspection system 100 and correlation of data with the substrates.

Micro-Crack Inspection Unit

The micro-crack inspection unit is designed to detect microscopic cracks in substrates, which, if undetected, would likely result in a broken wafer during processing. The micro-crack inspection unit may also detect material inclusions and holes, which can have a detrimental effect on both efficiency and quality of the final product. In one example, the micro-crack inspection unit utilizes bright field transmission near infrared wavelengths to detect contrast aspects of cracks present in substrates. In such an example, a substrate may be positioned above the bright field transmitter, such as a laser diode. The micro-cracks inside the substrate affect the infrared portion of the light that passes through the substrate. A CCD camera may be positioned to detect the optical transmission through the substrate. The resolution of the CCD camera determines the minimum crack width that can be detected. The crack size may be calculated by counting the associated dark gray pixels of the CCD camera image.

Alternatively, a high intensity flashable light may transmit light through the substrate to facilitate capturing of an image using a high-resolution CCD camera. A thin crack scatters the light and appears as a dark line on the captured image, while wider cracks let the light through the substrate and appear as white lines. The micro-crack lengths are calculated by measuring the number of pixels that represent the crack. Other methods of micro-crack inspection are also contemplated, including scanning acoustic microscopy, mechanical excitation, resonance ultrasonic vibration utilizing an external piezoelectric transducer in the frequency range of 20-90 kHz, electronic speckle pattern interferometry, lamb wave air coupled ultrasonic testing using an air-coupled transducer, and lock-in thermography.

The micro-crack inspection unit may detect 97 percent or more of cracks present on a substrate, including pinholes as small as 80 microns or less, with a false alarm rate of less than 0.3 percent. The micro-crack inspection unit determines crack location as well as the size of the crack (e.g., length and/or width of crack), while differentiating cracks from grain boundaries using algorithms that detect color differences (e.g., gray level), image width, and slopes of the gray level derivative. The micro-crack inspection unit may also measure the monocrystalline fraction of a substrate, in one example for cast wafers, when adapted to detect crystal fractions of substrates.

Examples of micro-crack inspection units suitable for use herein include the VINSPEC vision system from Vitronic Dr.-Ing. Stein Bildverarbeitungssysteme GmbH of Wiesbaden, Germany; the HE-WI-04 Wafer Inspection Module available from Hennecke Systems GmbH of Zulpich, Germany; the MCI-100 Microcrack Inspection unit from Semi-Lab Co. Ltd. of Budapest, Hungary; the GP MICRO-D .Cell inspection system available from GP SOLAR GMBH of Konstanz, Germany; and the TAURUS inspection system available from Intego GmbH of Erlangen, Germany. Other units, including those produced by other manufacturers, are also contemplated.

Thickness Measuring Unit

The thickness measuring unit is adapted to measure one or more of thickness, bow, warp, and resistivity of a substrate. In one example, the thickness measuring unit may include a near-infrared superluminescent diode (SLD) to facilitate substrate measurement. The thickness and of a substrate may be measured, for example, in 96 locations in a 3×32 area using 3 sensors (e.g., three near infrared SLDs), while the resistivity of a substrate may be measured, for example, in 32 locations in a 1×32 array. Resistivity may be measured, for example, using an eddy current sensor positioned centrally with respect to the substrate. The thickness measuring unit may determine substrate thickness with a repeatability of about 0.5 microns or less (e.g., multiple measurements of the same substrate are within 0.5 microns of one another), total thickness variation (TTV) with a repeatability of about 0.5 microns or less, substrate warp with a repeatability of about 1 micrometer or less, and resistivity with a repeatability of 1 percent or less. The thickness measuring unit may also determine a specific location (e.g., X, Y coordinate) of maximum and minimum thickness as well as maximum and minimum resistivity. It is to be understood that repeatability is the variation in measurements taken by the same instrument on the same substrate under the same conditions.

Examples of thickness measurement units suitable for use herein include the WMT-3 Thickness and Resistivity Tester available from SemiLab Co. Ltd. of Budapest, Hungary; the PV-1000 available from MTI Instruments Inc. of Albany, N.Y.; and the PV-R/PV-RT metrology platforms available from KITEC Microelectronic Technologie GmbH or Woerth-Hoerlkofen, Germany. Other units, including those produced by other manufacturers, are also contemplated.

Photoluminescence Unit

The photoluminescence unit is configured to detect defects, perform impurity measurements (e.g., percentage of impurities), and dislocation (e.g., crystallographic defect) measurements. Photoluminescence is the measure of radiative recombination when a sample is illuminated to excite excess carriers. As light generates excess carriers, their concentrations build up to values that depend on defects, impurities, and other recombination mechanisms in that region. Photoluminescence intensity is proportional to the carrier concentration: so, in general, bright areas indicate higher minority-carrier lifetime regions, whereas dark areas indicate higher defect concentration. Photoluminescence is a contactless technique, which allows it to be applied between many processing operations within the solar cell processing. During a photoluminescence inspection operation, a substrate is illuminated by a laser. Electrons are excited by photons, causing the electrons to move to the conduction band. As electrons fall back to the valence band, photons are emitted in a different wavelength. Impurities are characterized by a reduced band gap and are displayed on a graphical user interface as a dark zone, while grain boundaries are displayed as dark lines. In one example, illumination of a substrate is performed using a laser diode with 810-nm wavelength and up to 60 W of power over a 6"×6" area.

Figure 4:
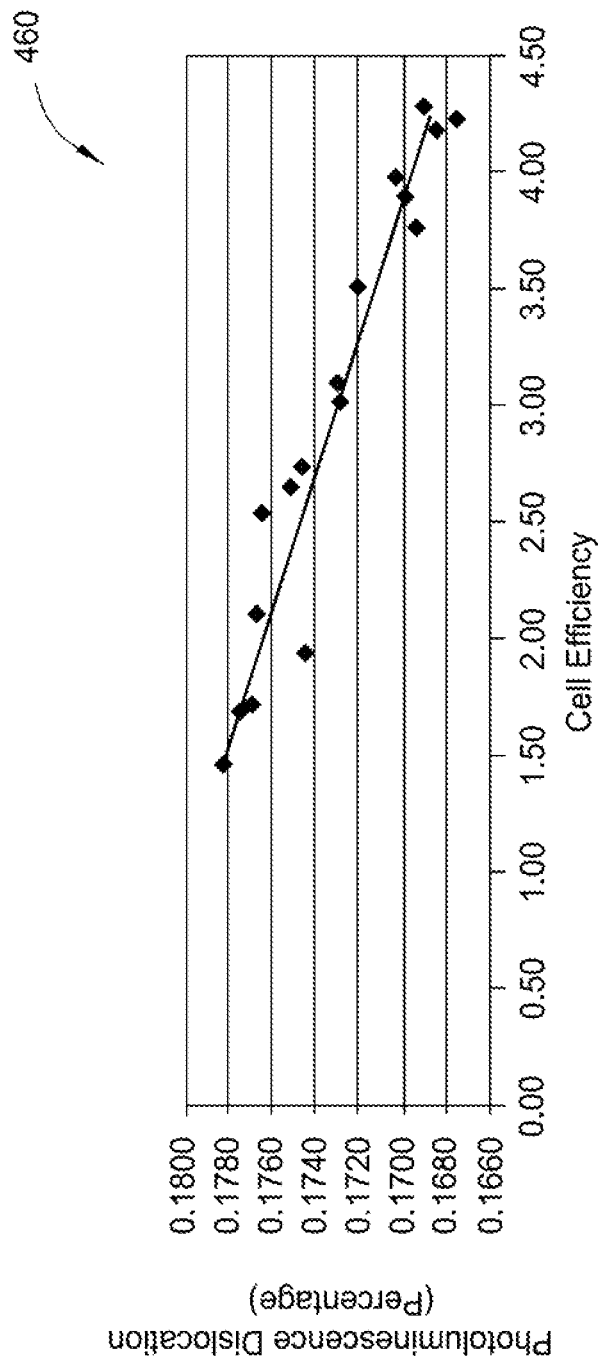
FIG. 4 illustrates relationship of between measured cell efficiency and photoluminescence dislocation percentage

The dislocation measurements are useful indicators of final cell efficiency for multi-crystalline silicon (cSi) substrates, as illustrate by the graph 460 of FIG. 4, and thus allow cell efficiency to be accurately determined before completion of the final device. FIG. 4 illustrates relationship of between measured cell efficiency and photoluminescence dislocation percentage. In one example, the cell efficiency as estimated using photoluminescence detection had a mean absolute error (MAE) of about 0.15 percent or less, such as 0.10 percent, compared to measured efficiency of finished devices.

Moreover, the photoluminescence unit facilitates control and development of gettering processes to ensure removal of a maximum amount of impurities by providing data in response to adjustments of gettering process variables. Additionally, the photoluminescence unit identifies substrate defects (e.g., location), and may quantify the performance impact of the defects through empirical algorithms. Furthermore, the photoluminescence unit facilitates removal of defects through identification of the defect locations, or alternatively, facilitates discarding of the substrates if the defects exceed a predetermined limit. Thus, unrecoverable substrates can be discarded before being subject to recovery techniques which would ultimately be unsuccessful, ultimately avoiding the time and expense of such processes.

Not only does the photoluminescence unit facilitate rejection of low quality substrates and eliminate wasted consumables and labor on non-sellable or non-recoverable substrates, but the photoluminescence unit also allows a manufacturer to plan and control substrate yield. Moreover, the photoluminescence unit also facilitates adjustment of processing parameters of a production line to achieve substrates having the greatest efficiency. In addition, the photoluminescence unit facilities sorting of substrates according to particular characteristics, such as efficiency, which may then be grouped into lots according to the characteristics.

Additionally, it is contemplated that the luminescence data of multiple substrates may be collected and stored on the yield analysis server 217 and utilized to facilitate a 3D virtual reconstruction of a brick or ingot from the sub-component substrates of the brick or ingot. The 3D reconstruction facilitates imaging of defects within the brick or ingot, which may lead to efficiency yield improvements through identification of consistent quality issues.

Substrates may come into a solar fabrication plant in lots, with each substrate having identifying information. The identifying information may be simply a sequence number of the substrate in a stack of substrates that arrive at the fabrication plant, for example, a slot number in a cassette. Additionally or alternatively, the identifying information may be a code or other designation that is laser written on the side of the substrate close to the edge of the substrate. The identifying information facilities identification of an ingot, and of a location within the ingot, from which a substrate came, as well as from which substrate manufacturer the substrate came. The fabrication plant software, such as software associated with the front end 101, the photoluminescence unit, the yield analysis server 217, or a combination thereof, facilitates tracking of the substrate throughout processing using the identifying information. Utilizing the identifying information, a 3D virtual reconstruction of a brink or ingot can be accomplished, since inspection data can be related to a particular substrate.

Examples of photoluminescence units suitable for use herein include the iLS-W2 inspection unit available from BT Imaging of Waterloo, NSW, Australia; the HE-PL-01 photoluminescence module available from Hennecke Systems GmbH of Zulpich, Germany; and the PLI-1001 photoluminescence inspection unit available from SemiLab Co. Ltd. of Budapest, Hungary. Other units, including those produced by other manufacturers, are also contemplated.

Geometry Inspection Unit

The geometry inspection unit may measure the length of a substrate with a repeatability of about 10 microns or less, and may measure the width of a substrate with a repeatability of about 40 microns or less. The chamfers of a substrate may be measured with a repeatability of about 40 microns or less, and the diagonal distance (e.g., corner to corner of a square or rectangular substrate) may be measured with a repeatability of about 40 microns less. Orthogonality of a substrate may be measured with a repeatability of about 0.1 degrees or less. The metrology unit ensures that substrates meet predetermined sizing requirements.

The geometry inspection unit may also be configured to perform on-the-fly stain detection across the top and bottom surfaces of a substrate, and additionally, may perform chip detection on the edges/sides of substrates. For example, the geometry inspection unit may detect chips and stains having a size as of about 150 microns or less, and side chips having a size of about 60 microns or less. Chips and stains of about 150 microns located on upper and lower surfaces of a substrate may be detected with a false alarm rate of less than 0.5 percent, while side chips having a size of about 60 microns may be detected with a false alarm rate of less than 0.5 percent. In contrast to previously-known chip inspection units which include a top mounted camera facing downward at a substrate, the geometry inspection unit of the present disclosure is configured with a U-shaped sensor for detecting side/edge chips.

Figure 5:
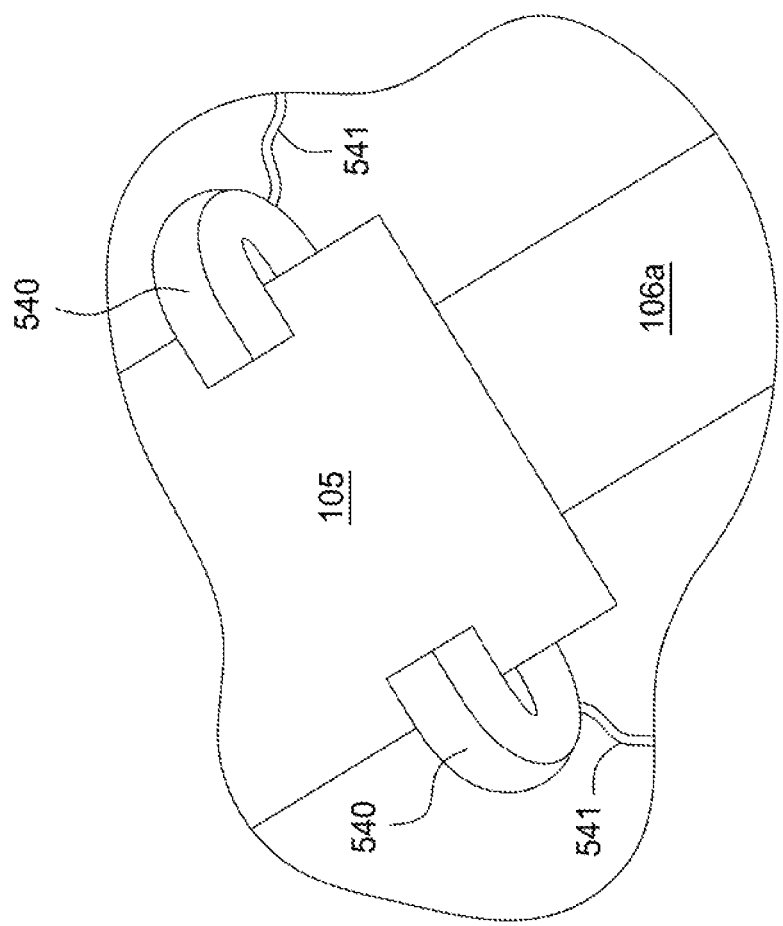
FIG. 5 illustrates detectors of a geometry inspection unit, according to one embodiment.

FIG. 5 illustrates a pair of U-shaped detectors 540 coupled to cables 541. The cables 541 may facilitate the transfer of power and data with respect to the U-shaped detectors 540. Each U-shaped detector 540 may include one or more light sources and one or more imaging devices, such as CCD cameras. A conveyor, such as the conveyor 106a, is adapted to transfer a substrate relative to and within an interior of the U-shaped detectors 540 to facilitate inspection of the substrate by U-shaped detectors 540. For example, opposite lateral edges of the substrate may be positioned within opposing U-shaped detectors 540 for inspection. Each U-shaped detector 540 is configured to inspect the outer 15 millimeters of the substrate adjacent the sides on the top and bottom surfaces as the substrate is moved relative thereto, and in addition, is configured to inspect the edge/side surface of the substrate. Thus, chips that do not have any impact on the top or bottom surfaces can be detected, in addition to chips that are located on the top or bottom surface adjacent the edge of a substrate.

Previously known inspection units are incapable of detecting chips that are located only on the sides of a substrate and do not have any impact on the upper surface of the substrate, due to the positioning of the inspection camera. The geometry inspection device may include an imaging device having a pixel size of about 15 microns to facilitate identification of the chips and imaging of the defects, in contrast to 40 micrometer pixel sizes of previous inspection systems.

Examples of geometry inspection units suitable for use herein include the SolVi(SV) WaferVision inspection unit from WithRobot of Seoul, South Korea; and the GP WAF-Q .CAM available from GP SOLAR GMBH of Konstanz, Germany. Other units, including those produced by other manufacturers, are also contemplated.

Saw Mark Detection Unit

The saw mark detection unit is configured to perform on the fly inspection of saw mark depth and location, and may inspect and identify saw marks of the following types: groove, step, and double step. The saw mark detection unit of the current disclosure analyzes both the thickness profile of a substrate, as well as the top/bottom profiles (e.g., topography) of the substrate. It is contemplated that filtering algorithms may be implemented to account for natural substrate motions/vibrations during transport, thus allowing saw mark detection to occur during substrate transportation. The saw mark detection unit is configured with a high resolution sensor having 600 micrometer depth repeatability, and a high scanning resolution (e.g., 3 microns on X-axis, or more than about 150,000 samples per substrate). The saw mark detection unit is capable of detecting the presence of "double saw marks" on a substrate, e.g., the presence of saw marks on both the top and bottom of a substrate. Previously utilized detection equipment, which relied solely on thickness profile measurements for saw mark detection, is often incapable of detecting the double saw marks.

Figure 6:
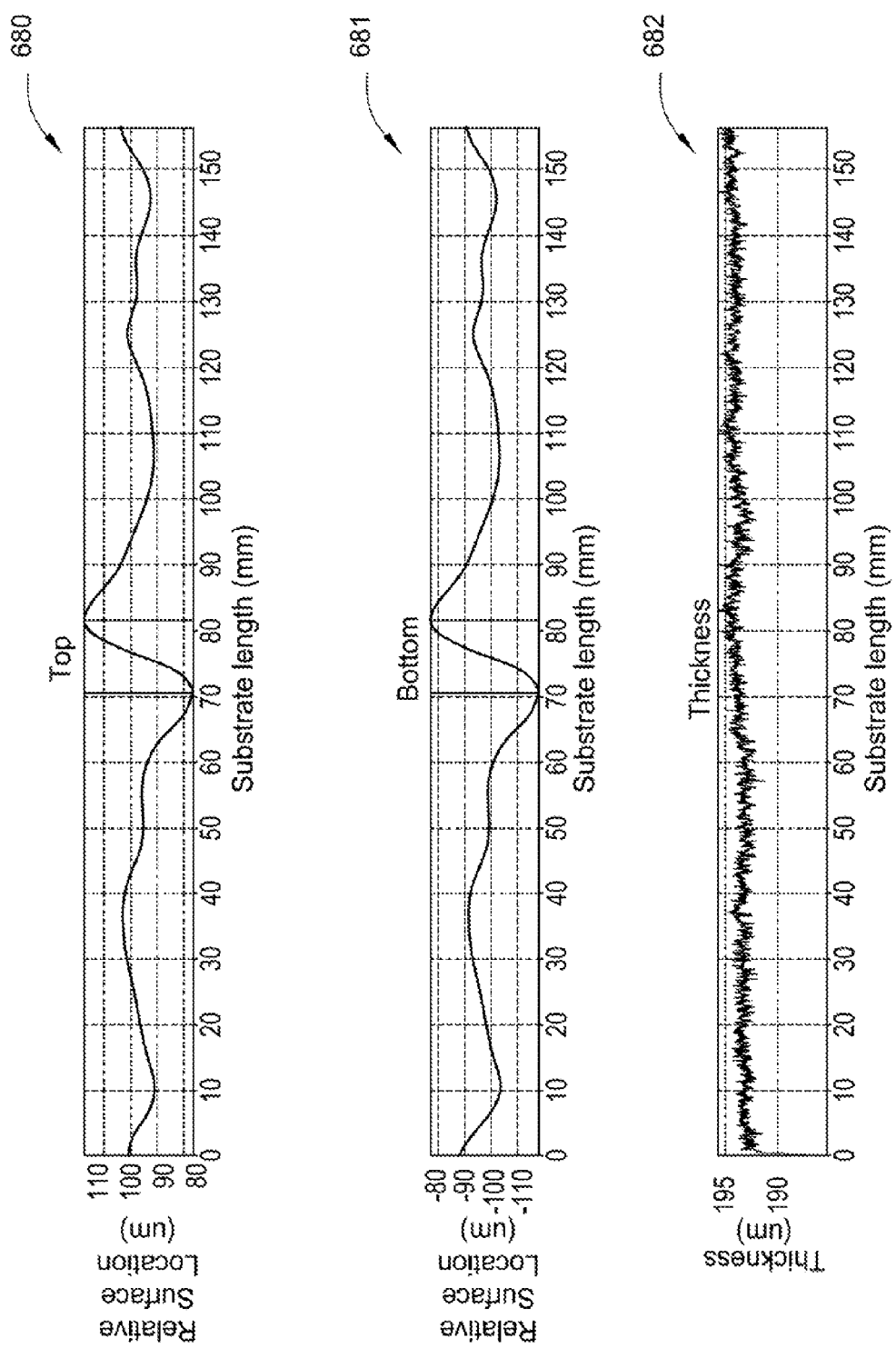
FIG. 6 illustrates the detection of saw marks on the top and bottom surfaces of a substrate, respectively, using surface profile analysis as well as thickness measurement.

FIG. 6 illustrates the detection of saw marks on the top and bottom surfaces of a substrate, respectively, using surface profile analysis as well as thickness measurement. Graph 680 illustrates the relative location of a top surface of a substrate across the length of the substrate. The variation shown between the 70-80 millimeter position indicates the presence of a saw mark on the top surface. Graph 681 illustrates the relative location of a bottom surface of the substrate across the length of the substrate. The variation shown between the 70-80 millimeter position indicates the presence of a saw mark on the bottom surface (e.g., a double saw mark). Graph 682 illustrates the thickness of the substrate across the length of the substrate. Graph 682 does not indicate the presence of a saw mark between the 70-80 millimeter position of the substrate. As illustrated, thickness measurements alone may not detect the presence of saw marks. However, the saw mark detection unit of the current disclosure utilizes thickness measurements as well as surface topography, and is thus able to more accurately detect the presence of saw marks, such as double saw marks. It is contemplated that the saw mark detection unit may utilize the measured substrate thickness from the thickness measurement unit, rather than repeating the thickness measurement.

Examples of saw mark detection units suitable for use herein include the SolVi(SV) Surface SawMark Inspection S/W available from WithRobot of Seoul, South Korea; and the PVS-5000 available from SemiLab Co. Ltd. of Budapest, Hungary; and the Solar Wafer Sawmark Inspector, Model 7231, available from Chroma ATE Inc., Taoyuan County, Taiwan. Other units, including those produced by other manufacturers, are also contemplated.

Minority Charge Carrier Inspection Unit

A minority charge carrier inspection unit provides periodic laser pulses to a substrate to excite the material of the substrate, thus generating free charge carriers which will then recombine at recombination centers. The transient generation/recombination process is monitored while reflected or emitted microwave power is recorded as a function of time. The amount of reflected or emitted microwave power is dependent upon the conductivity of the substrate, and therefore, the conductivity transient of the substrate can be evaluated, thus facilitating characterization of material quality.

Suitable minority charge carrier inspection units include the WML-1 and the WML-3, available from SemiLab Co. Ltd. of Budapest, Hungary; and the IL-800 Inline Wafer-Lifetime Testing unit available from Sinton Instruments of Boulder, Colo. Other units, including those produced by other manufacturers, are also contemplated.

Sorting Unit

The sorting unit includes a system of conveyors and bins, and is adapted to sort inspected substrates based upon one or more characteristics thereof as determined by the metrology units. In one example, the conveyor 106b (shown in FIG. 1) includes two parallel belts disposed longitudinally along a wafer transporting plane of the sorting unit. Each of the belts may be adapted to support substrates as the substrates are transferred through the sorting unit. The conveyor system may also include multiple sorting mechanisms 116 (shown in FIG. 1) to facilitate transferring of substrates in bins. The sorting mechanisms 116 may include one or more rollers or belts disposed orthogonally to and between the belts of the conveyor 106b, and optionally, one or more rollers positioned laterally outward of and parallel to the belts of the conveyor 106b. The sorting mechanisms 116 are actuatable from a position below the transporting surface of the conveyor 106b to a position above the transporting surface of the conveyor 106b.

The sorting mechanisms 116 are positioned proximate one or more bins 115 (shown in FIG. 1). As substrates are transported adjacent sorting mechanisms 116, the sorting mechanisms 116 actuate vertically to lift a substrate from the conveyor 106b, and transfer the lifted substrate to a bin 115 adjacent to the sorting mechanisms 116. The sorting mechanisms 116 may be adapted to transport substrates bi-directionally, thus, sorting substrates to bins 115 located on opposite sides of the conveyor 116b. In an alternative embodiment, each pair of sorting mechanisms 116 disposed between the main conveyor belts may be replaced with a single, actuatable conveyor that is sufficiently wide enough to support a substrate.

Figure 7:
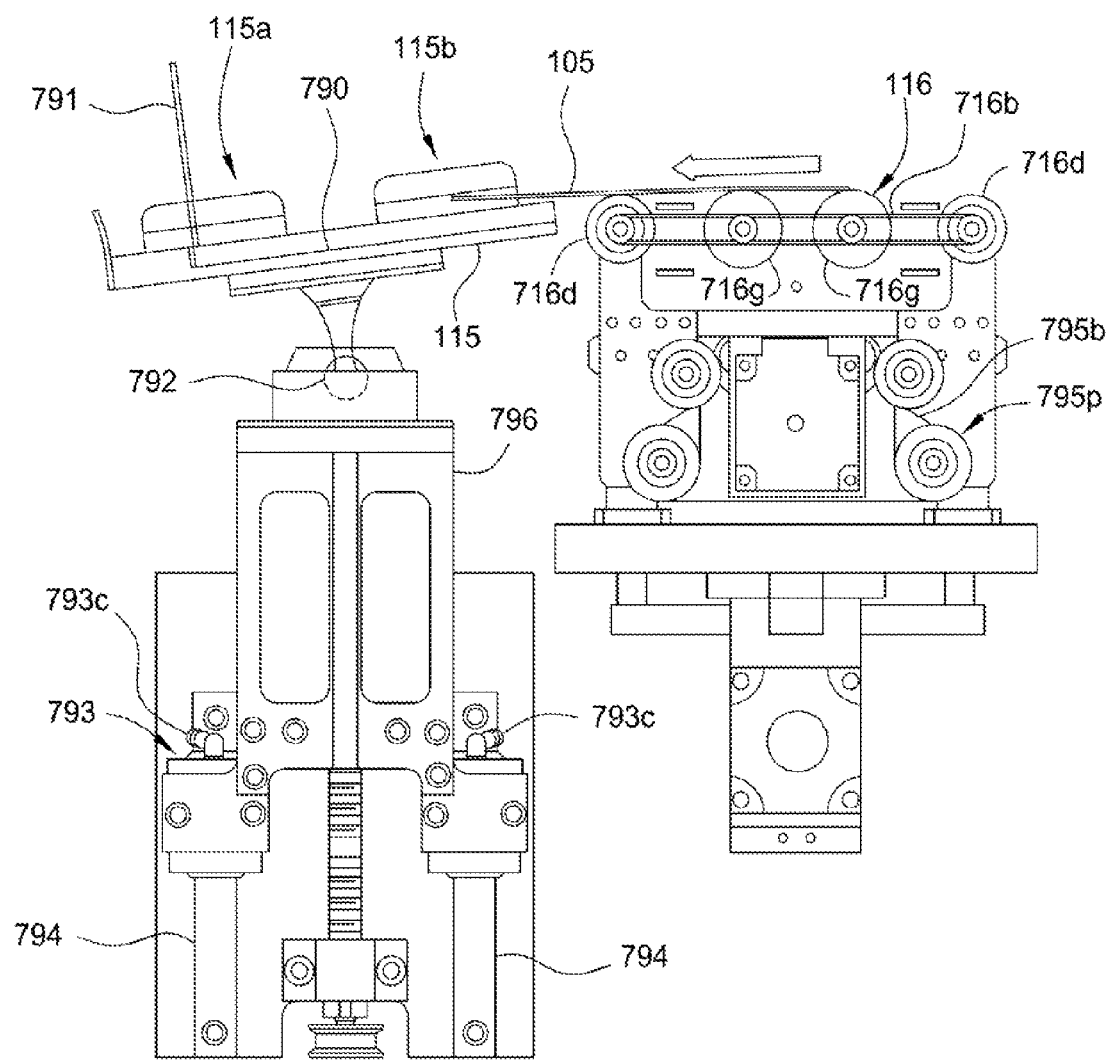
FIG. 7 illustrates transfer of a substrate to a bin, according to one embodiment.

FIG. 7 illustrates transfer of a substrate 105 to a bin 115, according to one embodiment. As illustrated in FIG. 7, the bin 115 is positioned below the upper surface of the sorting mechanism 116 to facilitate transfer of substrates 105 from the sorting mechanism 116 to the bin 115. Additionally, it is contemplated that a substrate receiving surface 790 of the bins 115 may be positioned at an angle with respect to the upper surface of the sorting mechanism 116 to facilitate transfer of the substrate 105 to the bin 115. In one example, the laterally outward edge 115a of the substrate receiving 790 surface of the bin 115 relative to the sorting mechanism 116 is disposed lower than the laterally inward edge 115b of the substrate receiving surface 790. Thus, as the substrate 105 is transferred to the bin 115, the substrate 105 moves down the declined substrate receiving surface 790 until contacting a support 791. An adjustable member 792 may be used to modify the angle of decline of the substrate receiving surface 790.

An actuator 793, such as a hydraulic or pneumatic actuator, is adapted to vertically actuate the bin 115 as directed by guides 794 to facilitate transfer of additional substrates 105 to the bin 115 as the bin 115 is loaded. One or more conduits 793c (two are shown) are adapted to provide fluid to facilitate operation of the actuator 794. A support 796 couples the actuator 793 to the bin 115. A system of belts 795b and pulleys 795p facilitates vertical actuation of the sorting mechanism 116. The sorting mechanism 116 may include one or more driving rollers 716d (two are shown), one or more guiding rollers 716g (two are shown), and a belt 716b.

Suitable sorting units include those produced by: Fortix Co., Ltd of Incheon, Korea; Hennecke Systems GmbH of Zulpich, Germany; SemiLab Co. Ltd. of Budapest, Hungary; and Chroma ATE Inc., Taoyuan County, Taiwan. Other units, including those produced by other manufacturers, are also contemplated.

Front End

The front end is adapted to receive one or more cassettes containing a plurality of substrates therein, for example, in a coin-stacked configuration. The cassettes may be disposed in cassette holders. In one example, the cassette holders support plural stacks of at least two cassettes which are independently indexed upwardly and downwardly. The one or more cassettes may be loaded and unloaded from the rear of a loading station into the cassette holders. Substrates within the one or more cassettes are transferred to the conveyor system 130 (shown in FIG. 1) via a robot which may be rotated or linearly translated in order to position substrates for delivery onto the conveyor system 130. It is contemplated that the front end may include more than one loading robot to facilitate increased substrate throughput.

Suitable front ends include those produced by: Applied Materials, Inc., or Santa Clara, Calif.; Fortix Co., Ltd of Incheon, Korea; the Stacker Unloader of Hennecke Systems GmbH of Zulpich, Germany; and Chroma ATE Inc., Taoyuan County, Taiwan. Other units, including those produced by other manufacturers, are also contemplated.

Embodiments herein may reference computers, servers, and the like. The computers, servers, and the like are generally designed to facilitate the control and automation of the inspection system 100 and components thereof. The computers and/or servers may include a central processing unit (CPU), memory, and support circuits. The CPU may be one of any form of computer processors that are used in industrial settings for controlling various system functions and support hardware (e.g., sensors, robots, motors, etc.), and monitor the processes (e.g., receive, collect, transfer, and analyze inspection data). The memory is connected to the CPU, and may be one or more of a readily available memory, such as random access memory (RAM), read only memory (ROM), floppy disk, hard disk, or any other form of digital storage, local or remote. Software instructions and data can be coded and stored within the memory for instructing the CPU. The support circuits are also connected to the CPU for supporting the processor in a conventional manner. The support circuits may include cache, power supplies, clock circuits, input/output circuitry, subsystems, and the like. One or more programs (or computer instructions) readable by the computers determines which tasks are performable on a substrate. Preferably, the programs are software that includes code to perform tasks relating to monitoring, execution and control of the movement and various process tasks being performed in the inspection system 100.

Benefits of embodiments described herein include customization and expansion of an inspection system. Moreover, manufacturers may inspect substrates at the beginning of fabrication process to facilitate the elimination of defective substrates prior to processing, thus avoiding wasted resources on unsatisfactory substrates, e.g., substrates which will result in an unsatisfactory final product. Additionally or alternatively, substrate manufacturers, such as wafer manufacturers, may inspect substrates before shipping the substrate to customers for processing, thus ensuring the shipped products meet certain quality control standards. The identification of defective substrates is facilitated by the accuracy of the inspection systems described herein. The comprehensive inspections performed by systems described herein facilitate improvement in device efficiency, as well as adjustments of processing parameters to improve yield and quality of processed substrates. Moreover, the embodiments of the present disclosure facilitate increased throughput, for example up to 3600 substrates per hour or more, while capable handling substrates having thicknesses less than 140 microns at a breakage rate less than 0.1 percent.

Additionally, embodiments of the disclosure enable manufacturers to set additional standards, particularly combinations of individual requirements, on incoming substrates, resulting in closer "binning" (e.g., sorting into bins based on the individual requirements) of the resulting solar cells. Solar cell manufacturers have difficulty binning substrates based on the broad difference in cell color and cell output using previously know technology. A panel manufacturer forms panels using cells having the same color appearance (aesthetics) and the same output (lowest performing cell dictates power out of the module), hence the sorting of substrates. If cell performance can be determined at the bare substrate level, then one can have tighter 'binning" of the cells actually made, resulting in better finished product, e.g., a product more closely meeting standards established by a manufacturer.

While the foregoing is directed to embodiments of the present disclosure, other and further embodiments of the disclosure may be devised without departing from the basic scope thereof, and the scope thereof is determined by the claims that follow.

What is claimed is:

1. An inspection system, comprising: a front end comprising a robot to unload substrates from a cassette and load the substrates onto a first conveyor; a modular unit comprising three or more metrology units linearly disposed along the first conveyor to inspect substrates on the first conveyor, the three or more metrology units comprising: a micro-crack inspection unit; a thickness and resistance measurement unit to measure substrate thickness with a repeatability of 0.5 microns or less; a photoluminescence unit; a geometry inspection unit to measure substrate length with repeatability of less than about 10 microns; and a saw mark detection unit; a yield analysis server to receive and process inspection data from the metrology units; and a sorting unit to sort substrates based upon the inspection data.

2. The inspection system of claim 1, wherein the metrology units are positioned in the sequential order of:
the micro-crack inspection unit; then
the thickness and resistance measurement unit; then
the photoluminescence unit; then
the geometry inspection unit; and then
the saw mark detection unit.

3. The inspection system of claim 1, wherein the sorting unit comprises:
a second conveyor;
a plurality of bins disposed laterally outward of edges of the second conveyor; and
a plurality of sorting mechanisms for transferring substrates from the second conveyor to the plurality of bins.

4. The inspection system of claim 3, wherein the second conveyor comprises two parallel belts disposed along the length of the sorting unit.

5. The inspection system of system of claim 1, wherein the thickness and resistance measurement unit has resistivity repeatability of 1 percent or less.

6. The inspection system of claim 1, wherein the yield analysis server is provided to generate a 3-dimensional virtual reconstruction of a brick or ingot from which the substrates were cut using inspection data received from the photoluminescence unit.

7. The inspection system of claim 1, wherein the geometry inspection unit has width repeatability of less than about 40 microns.

8. The inspection system of claim 1, wherein the geometry inspection unit has orthogonality repeatability of about 0.1 degrees or less.

9. The inspection system of claim 1, wherein the geometry inspection unit has corner-to-corner distance repeatability of less than 40 microns.

10. The inspection system of claim 1, wherein the geometry inspection unit has a false alarm rate of less than 0.5 percent when detecting stains having a size of about 150 microns.

11. The inspection system of claim 1, wherein the geometry inspection unit has a false alarm rate of less than 0.5 percent when detecting chips having a size of about 60 microns.

12. The inspection system of claim 1, wherein the geometry inspection unit includes a pair of U-shaped detectors.

13. The inspection system of claim 1, wherein the saw mark detection unit is provided to analyze a profile of a top surface and a bottom surface of a substrate.

14. The inspection system of claim 1, wherein the inspection system has a throughput of 3600 substrates per hour or more at a breakage rate of less than 0.1 percent.

15. An inspection system, comprising: a front end comprising a robot to unload substrates from a cassette and load the substrates onto a conveyor; a modular unit comprising three or more metrology units linearly disposed along the conveyor to inspect substrates on the conveyor, the three or more metrology units comprising: a micro-crack inspection unit; a thickness measurement unit to measure substrate thickness with a repeatability of 0.5 microns or less, and to measure substrate resistivity with a repeatability of 1 percent less; a photoluminescence unit; a geometry inspection unit to measure substrate length with repeatability of less than about 10 microns, the geometry inspection unit including a pair of U-shaped detectors; and a saw mark detection unit; a yield analysis server to receive and process inspection data from the metrology units and generate a 3-dimensional virtual reconstruction of a brick or ingot from which the substrates were cut using inspection data received from the photoluminescence unit; and a sorting unit to sort substrates based upon the inspection data.

16. The inspection system of claim 15, wherein the inspection system has a throughput of 3600 substrates per hour or more at a breakage rate of less than 0.1 percent.

17. The inspection system of claim 16, wherein the geometry inspection unit has a false alarm rate of less than 0.5 percent when detecting chips having a size of about 60 microns.

18. The inspection system of claim 16, wherein the geometry inspection unit has orthogonality repeatability of about 0.1 degrees or less.

19. The inspection system of claim 16, wherein the geometry inspection unit has width repeatability of less than about 40 microns.

20. An inspection system, comprising: a front end comprising a robot to unload substrates from a cassette and load the substrates onto a first conveyor; a modular unit comprising three or more metrology units linearly disposed along the first conveyor to inspect substrates on the first conveyor, the three or more metrology units comprising: a micro-crack inspection unit; a thickness measurement unit to measure substrate thickness with a repeatability of 0.5 microns or less, and to measure substrate resistivity with a repeatability of 1 percent less; a photoluminescence unit; a geometry inspection unit to measure substrate length with repeatability of less than about 10 microns, substrate width with repeatability of less than about 40 microns, and substrate orthogonality with repeatability of about 0.1 degrees or less, the geometry inspection unit including a pair of U-shaped detectors; and a saw mark detection unit; a yield analysis server to receive and process inspection data from the metrology units and generate a 3-dimensional virtual reconstruction of a brick or ingot from which the substrates were cut using inspection data received from the photoluminescence unit; and a sorting unit adapted to sort substrates based upon the inspection data, the sorting unit comprising: a second conveyor; a plurality of bins disposed laterally outward of edges of the second conveyor; and a plurality of sorting mechanisms for transferring substrates from the second conveyor to the plurality of bins.

* * * * *